United States Patent
Simola et al.

(10) Patent No.: US 9,040,756 B2
(45) Date of Patent: May 26, 2015

(54) PROCESS FOR PRODUCING 1,4-BUTANEDIOL BY HYDROGENATING DIALKYL MALEATE IN MIXED LIQUID/VAPOR PHASE

(75) Inventors: Flavio Simola, Monterotondo (IT); Marco Scarsella, Rome (IT); Paolo De Filippis, Rome (IT)

(73) Assignee: CONSER SPA, Rome (IT)

( * ) Notice: Subject to any disclaimer, the term of this patent is extended or adjusted under 35 U.S.C. 154(b) by 0 days.

(21) Appl. No.: 14/358,863

(22) PCT Filed: Nov. 25, 2011

(86) PCT No.: PCT/IT2011/000387
§ 371 (c)(1),
(2), (4) Date: May 16, 2014

(87) PCT Pub. No.: WO2013/076747
PCT Pub. Date: May 30, 2013

(65) Prior Publication Data
US 2014/0316146 A1  Oct. 23, 2014

(51) Int. Cl.
| C07C 31/18 | (2006.01) |
|---|---|
| C07D 307/00 | (2006.01) |
| C07D 307/20 | (2006.01) |
| C07C 29/17 | (2006.01) |
| C07C 29/149 | (2006.01) |
| C07D 307/08 | (2006.01) |
| C07C 67/303 | (2006.01) |
| C07D 307/33 | (2006.01) |

(52) U.S. Cl.
CPC ............. *C07C 29/172* (2013.01); *C07C 29/149* (2013.01); *C07C 29/177* (2013.01); *C07D 307/08* (2013.01); *C07C 67/303* (2013.01); *C07D 307/20* (2013.01); *C07D 307/33* (2013.01)

(58) Field of Classification Search
CPC ...... C07C 29/17; C07C 307/33; C07C 307/20
USPC .................................. 568/852; 549/325, 508
See application file for complete search history.

(56) References Cited

U.S. PATENT DOCUMENTS

| 2,110,488 | A | 3/1938 | Justemenet |
|---|---|---|---|
| 4,032,458 | A | 6/1977 | Cooley et al. |
| 4,172,961 | A | 10/1979 | Henery et al. |
| 4,584,419 | A | 4/1986 | Sharif et al. |
| 4,656,297 | A | 4/1987 | Kouha et al. |
| 4,751,334 | A * | 6/1988 | Turner et al. ............... 568/864 |
| 5,872,276 | A * | 2/1999 | Darsow ..................... 560/190 |
| 6,100,410 | A | 8/2000 | Tuck et al. |
| 6,137,016 | A | 10/2000 | Wood et al. |
| 6,191,322 | B1 | 2/2001 | Bertola |
| 6,239,292 | B1 | 5/2001 | Tuck et al. |
| 6,248,906 | B1 | 6/2001 | Bertola |
| 6,274,743 | B1 | 8/2001 | Tuck et al. |
| 6,288,245 | B1 | 9/2001 | Bertola |
| 6,350,924 | B1 * | 2/2002 | Fischer et al. .............. 568/864 |
| 6,433,193 | B1 | 8/2002 | Bertola et al. |
| 6,620,949 | B1 | 9/2003 | Sutton et al. |
| 6,844,452 | B2 | 1/2005 | Wood et al. |
| 6,936,727 | B2 | 8/2005 | Sutton et al. |
| 7,598,404 | B2 | 10/2009 | Backes et al. |
| 2007/0260073 | A1 | 11/2007 | Wood et al. |

FOREIGN PATENT DOCUMENTS

| BE | WO 99/35114 | * 7/1999 | ............ C07C 29/149 |
|---|---|---|---|
| CN | 101307042 A | 11/2008 | |
| CN | 101747149 A | 6/2010 | |
| WO | 82/03854 A1 | 11/1982 | |
| WO | 99/35114 A1 | 7/1999 | |
| WO | 99/52845 A1 | 10/1999 | |

OTHER PUBLICATIONS

International Search Report, dated Aug. 27, 2012, from corresponding PCT application.

* cited by examiner

*Primary Examiner* — Nizal Chandrakumar
(74) *Attorney, Agent, or Firm* — Young & Thompson

(57) ABSTRACT

A process for the production of 1,4-butanediol and tetrahydrofuran by catalytic hydrogenation of dialkyl maleates includes the following steps:

a) hydrogenating a stream of dialkyl maleate in a first stage of reaction over suitable catalysts to produce dialkyl succinate;

b) further hydrogenating the dialkyl succinate in a second stage of reaction, by using a different suitable catalyst, for producing mainly 1,4-butanediol, together with gamma-butyrolactone and tetrahydrofuran as co-products. In both stages of reaction the conditions, as hydrogen/organic feed ratio, pressure and temperature, are such to maintain the reactors in mixed liquid/vapor phase.

8 Claims, 2 Drawing Sheets

PROCESS FOR PRODUCING 1,4-BUTANEDIOL BY HYDROGENATING DIALKYL MALEATE IN MIXED LIQUID/VAPOR PHASE

SUMMARY OF INVENTION

A process is described for the production of 1,4-butanediol and tetrahydrofuran by catalytic hydrogenation of dialkyl maleates. The process consists essentially in the following steps:
a) hydrogenating a stream of dialkyl maleate in a first stage of reaction over suitable catalysts to produce dialkyl succinate;
b) further hydrogenating the dialkyl succinate in a second stage of reaction, by using a different suitable catalyst, for producing mainly 1,4-butanediol, together with gamma-butyrolactone and tetrahydrofuran as co-products.

In both stages of reaction the conditions, as hydrogen/organic feed ratio, pressure and temperature, are such to maintain the reactors in mixed liquid/vapor phase.

FIELD OF DISCLOSURE

Embodiments disclosed herein relate generally to processes and equipment to produce 1,4-butanediol, together with gamma-butyrolactone and tetrahydrofuran as co-products, by reacting a feed, consisting of alkyl maleates, with hydrogen gas in a two stages reaction over suitable catalysts.

BACKGROUND OF THE INVENTION 1,4-butanediol (BDO) is a versatile chemical intermediate, thanks to its terminal, primary hydroxyl groups and to its chemical resistant nature.

BDO is an important raw material in the synthesis of technically relevant polymers such as thermoplastic urethanes and polyesters, mainly polybutylene terephthalate (PBT), polyester plasticizers, paints, coatings and adhesives.

In the recent years the largest consumer of BDO is tetrahydrofuran (THF), used to produce poly-tetramethylene ether glycol (PTMEG) a key raw material for spandex fibers. Substantial quantities of BDO go into the manufacture of gamma-butyrolactone (GBL) which is in turn used to manufacture N-methyl-pyrrolidone (NMP) and other pyrrolidones.

There are a number of routes to manufacture BDO: the first commercial route was the Reppe process from acetylene and formaldehyde. Other technologies include the production from butadiene, from propylene oxide, from allyl alcohol and more recently through biotransformation process.

Thanks to the availability and low cost of the raw material, in the last twenty years and in the next future the processes based on butane/maleic anhydride tend to dominate the market.

The processes based on butane/maleic anhydride comprise two main groups.

The first group includes all the processes based on the esterification of the maleic anhydride by methanol, ethanol or other alcohols and the following hydrogenation of the dialkyl ester, usually as dimethyl maleate (DMM), to butanediol and/or, depending on the conditions of pressure and temperature and on the catalyst, to tetrahydrofuran and gamma-butyrolactone.

The second group on the contrary includes the processes based on the direct hydrogenation of the maleic anhydride or maleic acid to BDO and/or THF and GBL. Even if theoretically these processes appear to be simpler, with fewer processing steps (both the maleic anhydride purification and the esterification are not necessary), in the industrial application they met with poor success, probably due to the high cost of the catalyst and of the sophisticated materials of construction necessary in presence of maleic acid at high temperature.

Considering again the processes of the first group based on the esterification of the maleic anhydride, another distinction can be made between the processes based on the hydrogenation in vapor phase and the processes based on the hydrogenation in mixed liquid/vapor phase.

The new process introduced in the present invention belongs to the hydrogenation processes of diesters of the maleic anhydride in mixed phase.

Irrespective of the vapor or mixed phase, it is believed that the reaction of dimethyl maleate to 1,4-butanediol proceeds through at least two intermediates, as follows:

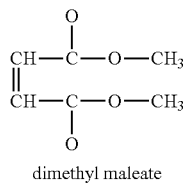

dimethyl maleate $+H_2$ ($\Delta H_{R(gas)}$ = -30.31 Kcal/mole)
Hydrogenation reaction

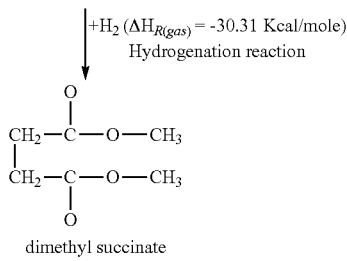

dimethyl succinate $+2 H_2$ ($\Delta H_{R(gas)}$ = 0.60 Kcal/mole)
Hydrogenolysis reaction

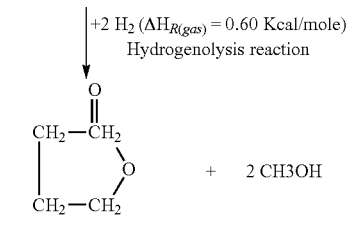  + 2 CH3OH gamma-butyrolactone $+2 H_2$ ($\Delta H_{R(gas)}$ = -11.391 Kcal/mole)
Hydrogenolysis reaction

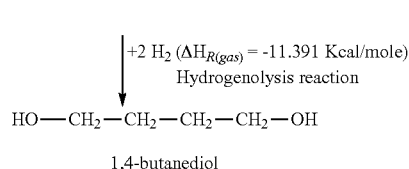

1,4-butanediol $-H_2O$ ($\Delta H_{R(gas)}$ = 0.17 Kcal/mole)
Dehydration reaction

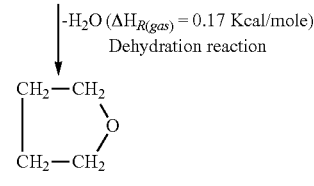

tetrahydrofuran

In conclusion, 1,4-butanediol, tetrahydrofuran and gamma-butyrolactone are products of reaction which are converted one to another by addition/subtraction of hydrogen and/or water. The products distribution may be changed by adjusting the operating parameters of the hydrogenolysis reaction or the type of catalysts.

In the prior art several inventions have been applied on the hydrogenation of maleic anhydride esters to produce 1,4-butanediol.

U.S. Pat. No. 2,110,488 can be considered the first application concerning the hydrogenation of an ester of aliphatic carboxylic acids to produce aliphatic alcohols using a catalyst consisting of copper oxide and chromium oxide, within a temperature range from 250 to 300° C. and within a pressure range from 150 to 300 atmospheres.

On the other hand U.S. Pat. No. 4,032,458 is the first application on the production of 1,4-butanediol, where a solution containing maleic acid is first subject to esterification by a monohydric alcohol and the dialkyl ester of maleic acid is hydrogenated in a two reaction steps, the first step to saturate the double bond present in the maleic acid and the second step to produce 1,4-butanediol and the monohydric alcohol. Both reaction steps uses a copper-chromite catalyst. Reaction temperatures are in the range from 100 to 300° C., reaction pressures from 172 to 241 barg, being the catalyst dissolved in slurry.

U.S. Pat. No. 4,172,961 is another application of copper chromite catalyst in slurry, to hydrogenate dibutyl butoxy succinate to 1,4-butanediol.

WO patent 82/03854 is a generic process to hydrogenate a carboxylic acid ester in vapor phase with a catalyst comprising a mixture of copper oxide and zinc oxide. One of the several possible applications concerns the production of 1,4-butanediol from an ester of maleic, fumaric or succinic acid.

U.S. Pat. No. 4,584,419 consists in a process to hydrogenate an ester of maleic anhydride to butanediol in vapor phase in the presence of a copper chromite catalyst.

U.S. Pat. No. 4,656,297 is another process to produce butanediol by the hydrogenation in vapor phase of dimethyl-succinate with copper chromite catalyst, by adding methanol to the ester feed.

U.S. Pat. No. 4,751,334 is also an hydrogenation process in vapor phase with Cu—Cr or Cu—Zn oxide catalyst, to produce 1,4-butanediol from diethyl maleate in two or three adiabatic hydrogenolysis zones in series.

U.S. Pat. No. 5,872,276 refers to a process to hydrogenate dialkyl maleate to dialkyl succinate in liquid phase at a pressure of from 50 to 400 bar, at temperature of from 30 to 160° C. and at hydrogen/feed molar ratio from 20 to 40. The catalyst consists of pressed powders of the elements of the iron subgroup with addition of elements of transition groups IV or V, having particular compressive strength and internal surface area.

WO patent 99/52845 represents a process for producing BDO by vapor phase hydrogenation of different types of feed, including dimethyl maleate, characterized by the addition of carbon monoxide to the reaction.

U.S. Pat. Nos. 6,100,410, 6,239,292, 6,274,743, 6,350,924 and 6,433,192 describe different special integrations between a maleic anhydride plant and a BDO production plant, wherein the maleic anhydride absorbed in an organic solvent is first esterified and the resulting maleic ester is stripped by a stream of hydrogen and then subject to an hydrogenation in vapor phase.

U.S. Pat. Nos. 6,137,016 and 2007/0260073 provide a process for the purification of BDO containing minor amount of cyclic acetal, by hydrogenating the butanediol in presence of minor amount of water and under conditions of temperature and pressure typical of the liquid/vapor reactions.

U.S. Pat. No. 6,191,322 is a process for the production of BDO by mixed phase catalytic hydrogenation of gamma-butyrolactone or succinic anhydride esters or their mixtures in two catalytic steps in series with injection of cold hydrogen between the reaction stages, at pressure of from 75 to 90 bar and temperature between 160 and 250° C. The catalyst can be selected between copper and zinc oxide or copper chromite.

U.S. Pat. No. 6,248,906 is a process where the maleic anhydride ester is subject to two subsequent hydrogenation steps, where the primary hydrogenation produces mainly GBL and THF and the secondary hydrogenation converts a fraction of GBL to BDO.

U.S. Pat. No. 6,288,245 teaches a process to convert the BDO produced by vapor phase hydrogenation of maleic ester to THF through a second stage reactor containing silica-alumina catalyst.

U.S. Pat. No. 6,433,193 refers to an integration between maleic anhydride and butanediol productions, where the maleic anhydride is recovered by absorption in gamma-butyrolactone and the resulting mixture of maleic anhydride and GBL is subjected to an hydrogenation step under conditions favoring the formation of THF and GBL.

U.S. Pat. No. 6,620,949 is another process of integration where the maleic anhydride used to produce BDO, GBL and THF is produced by partial condensation of the vapor effluent from a maleic anhydride catalytic oxidation reactor.

U.S. Pat. No. 6,844,452 is a hydrogenation process in vapor phase for production of BDO and THF from dimethyl or diethyl maleate, characterized by three hydrogenation zones in series using different catalysts, such arrangement permitting to accept minor amounts of acidic material in the feed, to enhance the yields of THF and to reduce the formation of cyclic acetals.

U.S. Pat. No. 6,936,727 refers to a particular scheme of vapor phase hydrogenation, using catalyst and conditions favorable to the formation of tetrahydrofuran, characterized by the liquid feed which is divided in two parts fed separately to two subsequent vaporizer/reactor systems, allowing in this way an overall lower circulation of hydrogen to maintain the reactor feed above its dew point temperature.

CN patent 101307042 relates to a method for producing BDO together with THF and GBL, by using two catalyst bed layers, the first containing copper oxide and copper chromite or zinc oxide with one among Ba, Mg, Ti, Ce, Si, Zr and Mn oxide additive, the second containing copper oxide, alumina and one of the above described additive.

The aim of the U.S. Pat. No. 7,598,404 is the same of the above mentioned U.S. Pat. No. 6,936,727: in a process targeted to producing mainly tetrahydrofuran, the feed is first hydrogenated in a pre-reactor zone comprising catalyst which favors the carbon double bond saturation, i.e. the production of dimethyl succinate from dimethyl maleate. In this way the heat of reaction may be utilized in the evaporation of some of the liquid feed. Accordingly to the patent, in the second reaction zone, where THF and optionally diol and/or lactone are produced, the reaction occurs strictly under conditions of complete vaporization.

CN patent 101747149 discloses a method for preparing BDO by two stages hydrogenation in series by using maleic acid dialkyl ester, where the effluent from the first reaction step is cooled and separated in two phases and the resulting liquid product is contacted again with hydrogen in the second hydrogenation section.

Most of the above mentioned and other patents on the production of butanediol by hydrogenation of a dialkyl maleate, refers to a reaction in vapor phase. The operation in vapor phase at high pressure needs a large amount of recirculating hydrogen rich gas.

Moreover the conversion of DMM in a single reactor, where both the hydrogenation (double bond saturation) and the hydrogenolysis reactions occur at the same time, being the hydrogenation reaction the more exothermic step and also the quicker as rate of reaction, causes localized high temperatures (hot spot) in the first part of the catalytic bed difficult to control and producing unwelcome by-products, butanol and other, and risk of catalyst decay.

The already mentioned U.S. Pat. No. 7,598,404 refers at page 3: In conventional vapour phase reactions with hydrogen the capital and operating costs, particularly energy and other utilities requirements, are largely determined by the flow rate of the gas feed to the vaporiser . . . . The size of the compressors, heat exchangers and interconnecting pipework is dictated by the cycle gas flow rate as is the power required for compression and the heat required to be added to the reactor feed and removed from the reactor product. There is therefore a strong incentive to minimize the cycle gas flow rate within a particular process.

It is clear the reduction of the cycle gas below a certain limit, causes the reaction to be any more in vapor phase and to enter in the mixed liquid/vapor conditions. This operation with a reduced gas circulation, even if of course it is advantageous both as capital and operating cost, owing to the high exothermic effect of the hydrogenation reaction, results in a more difficult control of the reaction temperature. In fact, as already mentioned, excessive temperature of the reaction involves both an higher formation of undesired by-products and a reduced life of the catalyst. The by-products are certainly cause of reduced efficiency (higher consumption of raw materials and utilities) and, in some cases, are detrimental for the quality of the product.

The above mentioned U.S. Pat. No. 6,191,322 is one of the very few patent for the production of BDO in mixed phase. The patent solves the problem connected to the temperature control, first by using as feedstock an already partially hydrogenated product, i.e. gamma-butyrolactone or dimethyl succinate or a mixture of both compounds, second by using a multistage reactor and by cooling down the mixture between the reaction stages by injecting cold hydrogen.

It is clear that the main limitation of this patent is related to the type of feedstock, which needs a further separate hydrogenation plant to transform dimethylmaleate into dimethylsuccinate or gamma-butyrolactone.

It is object of the present invention a method to produce 1,4-butanediol from dialkyl maleates in a single hydrogenation plant, by avoiding the expensive process in vapor phase.

SUMMARY OF THE DISCLOSURE

Aim of the present invention is to propose a process for the production of 1,4-butanediol and tetrahydrofuran and, optionally, gamma-butyrolactone by catalytic hydrogenation of dialkyl maleates.

The process consists essentially in the following steps:
a) hydrogenating a stream of dialkyl maleate in a first stage of reaction over a suitable catalyst to produce dialkyl succinate;
b) further hydrogenating the dialkyl succinate in a second stage of reaction, by using a different suitable catalyst, for producing mainly 1,4-butanediol, together with gamma-butyrolactone and tetrahydrofuran as co-products.

In both stages of reaction the conditions, as hydrogen/organic feed ratio, pressure and temperature, are such to maintain the reactors in mixed liquid/vapor phase.

In the preferred embodiment of the present invention the catalyst used in the first step of hydrogenation shall have to following characteristics:
i) high selectivity to the saturation of the carbon double bond and very low selectivity to the hydrogenolysis;
ii) high activity to the saturation of the carbon double bond even at moderate temperature.

By using a catalyst having the above described characteristic, besides the other economic advantages already described due to the reaction in mixed liquid/vapor phase rather than in vapor phase, the following further advantages are achieved:
a) the heat released during the first step of reaction is only limited to the saturation of the carbon double bond; by using a controlled amount of recycle hydrogen, the increase of temperature in a fixed bed reactor is also easily maintained under control.
b) by properly controlling the inlet temperature of the reaction mixture, dialkyl maleate and recycling hydrogen rich gas, the outlet temperature from first reaction step may match the inlet temperature of the second stage of the reaction, where most or all the hydrogenolysis reactions take place.
c) all the heat of reaction of the first hydrogenation step is used for pre-heating at the proper temperature the reactive mixture entering the second stage.
d) the heat content of the liquid-gas mixture from the second stage of reaction, at a temperature between 180 to 230° C., is first used to generate low pressure steam, which may be used in other sections of the plant, for instance for the distillation of DMM or for the purification of the products, BDO, THF and, if required, GBL. Then the effluent heat is used to preheat of the mixed phase feedstock, DMM plus hydrogen, up to the inlet temperature of the first stage of reaction, which, as above mentioned, may be moderate (between 80 to 130° C.). No external heat source is needed.

In conclusion the two stages reaction system, as proposed in this invention, not only cuts to nil the external energy consumption, normally not negligible in the conventional processes in vapor phase, but also permits the production and the export of steam from the reaction system, by making the best of the intrinsic exothermic heat of the hydrogenation reactions. Moreover the proposed solution permits a better control of hot spot temperatures and a more selective process, with reduced amount of by-products.

In another embodiment of this invention, the temperature profile of the second stage of reaction can be improved and flattened, by injecting moderate amounts of cold hydrogen, withdrawn from the discharge of the recycle compressor, and sent, without any heat recovery, in intermediate points of the fixed bed second stage of reaction.

Examples of suitable catalysts to be used in the first stage include low content palladium catalysts supported on carbon or on alumina.

Examples of suitable catalysts to be used for hydrogenolysis in the second stage include copper containing catalysts, such as copper-chromite catalysts or copper-zinc oxide catalysts.

To an extent surprisingly more favourable than expected, the tests produced using the above described reaction in mixed phase and in two steps showed that the formation of the by-product cyclic acetal, the 2-(hydroxybutoxy)-tetrahydrofuran, which represents a particularly undesired impurity due to its boiling point very close to that of BDO, is considerably reduced compared to other similar processes in vapor phase. This represents a further and not negligible advantage of the present invention. On the other hand the already mentioned US patent 2007/0260073 by Davy Process Technology Ltd. teaches that the reduction of acetal may be achieved by contacting in liquid phase with a stream of hydrogen and in presence of catalysts of the same type described in the present invention the butanediol produced, normally in vapor phase, in another hydrogenolysis reactor. The present invention reaches a still better result, in terms of acetal contamination, simply by operating the hydrogenolysis reaction in mixed liquid-gas phase, without any need of additional purification step in liquid phase.

Another aspect of this invention became manifest during the execution of the laboratory tests. In an industrial plant the total reaction gas, used in large excess respect the stoichiometric amount, is mainly made by recycle gas, originated in the low temperature (30 to 60° C.) liquid-gas separator located after the cooling of the second stage reaction effluent. In the second stage of reaction some tetrahydrofuran is produced together with a stoichiometric amount of water. Being such water much lighter, as boiling point, than the main product (BDO), most of the water remain in vapor phase and, therefore, the recycle gas, circulated back to the first stage of reaction by a compressor, is saturated with vapor water.

In the laboratory tests, where the equipment arrangement is simpler than in the industrial plant, all the reaction gas is formed by high purity gas from hydrogen cylinder. In order to reproduce the industrial plant performances, some tests have been repeated by adding to the hydrogen stream a calculated amount of steam. Surprisingly, in the tests with addition of steam the THF/BDO ratio was much lower, around half, compared to the tests with anhydrous hydrogen. This feature may be used when the desired final product from the plant is mainly or only THF rather than BDO: by removing water from the recycle gas, the yield in THF may be in some extent increased. The water removal from the recycle gas may be accomplished by contact with a solid adsorbent of several types. A possible adsorbing agent is a standard zeolite used for the dehydration of gases.

Alternatively the water removal from the hydrogen rich gas can take place by contacting it in a absorption column with an organic solvent having high boiling point and hygroscopic tendency, as for instance triethylene glycol. The preferred type of liquid absorbent is however one of the products from the plant, including butanediol or gamma-butyrolactone, recycled back from the product purification system of the plant. The tetrahydrofuran on the contrary in not considered a right absorbent, both since it is a volatile product (the boiling point is only 65° C.) and since it is quite difficult to separate from water by distillation, by forming the two components an azeotropic mixture. Beside the increased yields in THF, the water removal from the recycle gas may also contribute to reduce the deterioration of the catalysts and to increase their life time.

The process of this invention allows to modify the relative ratios of butanediol, tetrahydrofuran and gamma-butyrolactone.

The THF/BDO ratio may be modified, besides by means of the above described moisture removal from the recycle gas, even by subjecting either the crude or the refined butanediol and either in presence or without hydrogen to a process of dehydration at moderate temperature, 120 to 250° C., which may occur by contact with an acidic catalyst of the silica-alumina type or, if applied to the purified butanediol, of the polymer-based resin with sulfonic acid group.

Moreover the THF+GBL/BDO ratio may be also increased by lowering the pressure of the hydrogenation reaction.

A right combination of moisture removal, reduced operating pressure and acid catalyst bed may contribute to reach the desired ratio THF/BDO. Moreover, also the production of gamma-butyro-lactone may be controlled from zero to a certain amount, by adjusting its recycle rate, between full recycle to zero recycle, from the purification to the hydrogenation section.

The overall Hydrogenation reaction conditions and performances relevant to the this invention are summarized in the attached Table 1.

TABLE 1

| Reactors conditions and performances | |
|---|---|
| Pressure | 30 to 80 bar |
| Temperatures | |
| $1^{st}$ stage inlet | 80 to 130 ° C. |
| $2^{nd}$ stage inlet | 160 to 190 ° C. |
| Ratio Hydrogen/organic feed (molar) | 30 to 60 |
| Liquid Hourly Space velocity (LHSV) | |
| $1^{st}$ stage | 0.5 to 2.0 |
| $2^{nd}$ stage | 0.1 to 0.3 |
| DMM conversion | higher than 99.9% |
| Selectivity (BDO/THF/GBL) | higher than 95% |

DETAILED DESCRIPTION OF THE INVENTION

Figure 1:
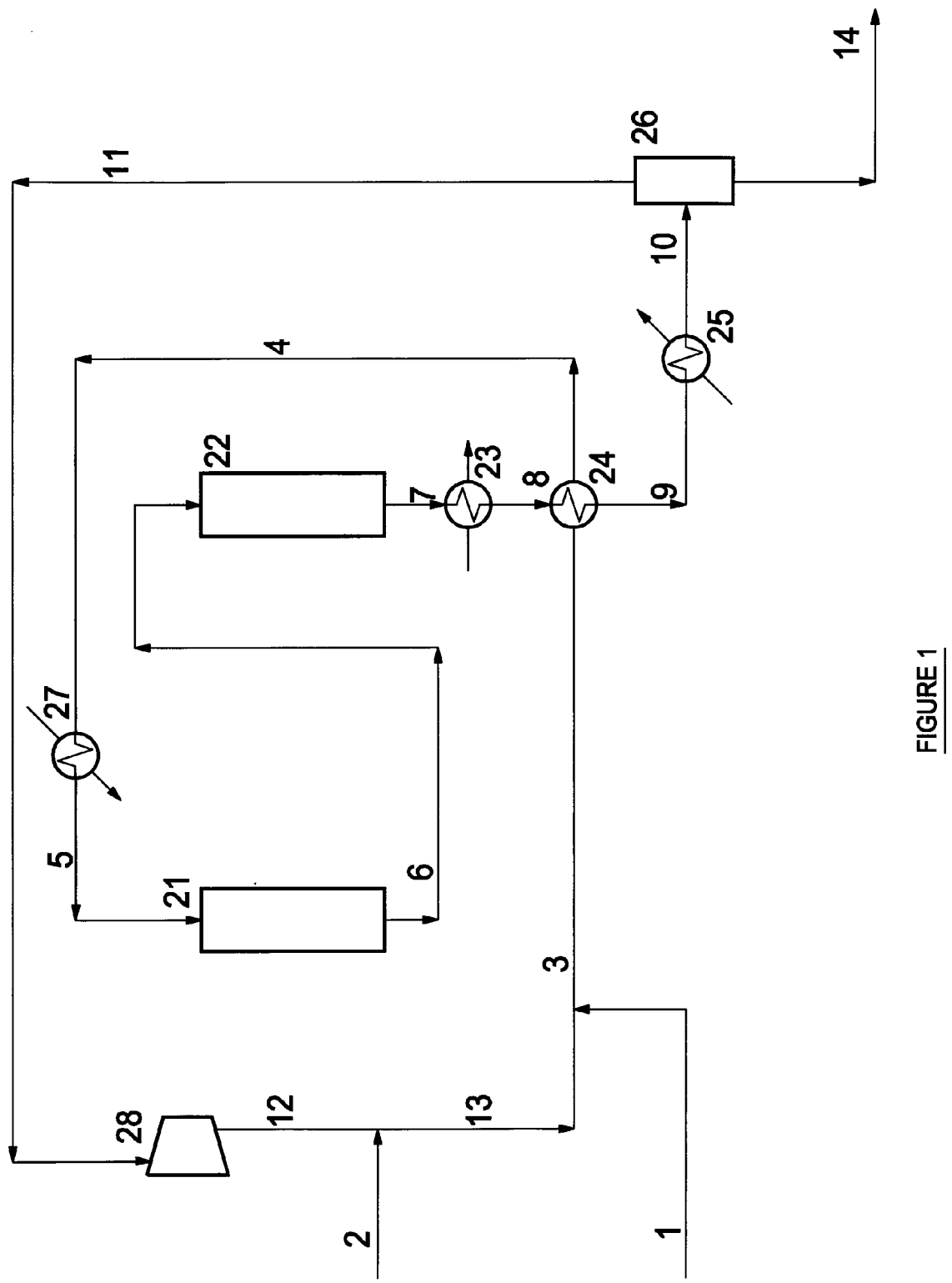
FIG. 1 is a simplified process flow diagram of the hydrogenation system, as described in the summary of the disclosure points (a), (b), (c) and (d), to produce 1,4-butanediol and, optionally, gamma-butyrolactone and/or tetrahydrofuran by catalytic hydrogenation of dialkyl maleates.

FIG. 1 illustrates a plant for the production of BDO and, optionally GBL and THF, by catalytic reaction of a dialkyl maleate, typically dimethyl maleate, with hydrogen in mixed liquid-vapor phase.

The dimethyl maleate, produced by catalytic esterification of maleic anhydride, is fed as stream 1 in liquid phase. Stream 1 may also contain, beside DMM, a minor amount of unconverted DMS recycled back from the purification section of the plant, normally in mixture with some amount of GBL. Stream 1 is mixed with stream 13, which represents the mixture of the fresh hydrogen stream 2 with the reaction recycle gas stream 12.

The resulting stream 3 is therefore a mixed liquid/vapor fluid. It is first preheated in the heat exchanger 24, by recovering heat from the effluent stream 8 of the second stage hydrogenation reactor 22, and then in the heat exchanger 27, using condensing low pressure steam as heating medium.

This heat exchanger 27 is used for temperature control reason particularly during the start-up of the plant; during the normal steady operation of the plant, it could be disconnected or by-passed. By using peculiar start-up procedures, the heat exchanger 27 could be even eliminated. The outlet stream 5 from the exchanger enters the first stage of reaction 21. It is a downflow fixed bed adiabatic reactor, containing a specific catalyst highly selective for the saturation of the carbon double bond contained in the dialkyl-maleate.

In the catalyst bed of reactor 21 the dimethyl maleate is transformed in dimethyl succinate with very high conversion and selectivity. This reaction is highly exothermic and therefore the outlet temperature of the effluent stream 6 is somewhat higher than the temperature of the inlet stream 5. In a preferred embodiment of this invention, the reaction system is designed in a way that the outlet temperature of the first reactor stage matches the inlet temperature of the second reaction stage and, therefore, no heat exchanger is included in the design of the system.

The effluent from the reactor first stage 6 under controlled temperature enters the second stage reactor 22. It is also a downflow fixed bed adiabatic reactor, containing a catalyst different from the first stage and, more specifically, a catalyst suitable for the hydrogenolysis of the dimethyl succinate to 1,4-butanediol; depending from the conditions of pressure and temperature, together with BDO, variable amounts of gamma-butyrolactone and/or tetrahydrofuran can be produced.

Product stream 7 from the reactor is first cooled in the heat exchanger 23. The heat exchanger 23 is a steam generator, preferably of the kettle type with the production of steam inside the shell of the exchanger. It could be, as alternate case, a natural circulation exchanger, where the boiler feed water used to produce steam is fed to an external vessel and a natural thermosiphon circulation is generated between the vessel and the boiler.

The outlet stream 8 from the heat exchanger 23 is passed to the already described interexchanger 24. The outlet stream 9 is further cooled in the heat exchanger 25, which is without distinction a water cooler or an air cooler.

The cooled stream 10 enters the separator vessel 26, where the crude liquid product 14, containing mostly BDO with lower percentages of gamma-butyrolactone, tetrahydrofuran, methanol, water, unreacted dimethyl succinate and impurities, is separated from the vapor phase stream 11, consisting essentially in hydrogen, with lower amounts of methanol, tetrahydrofuran and water. The gaseous stream 11 is then recycled back via the compressor 28, which differential pressure corresponds to the total pressure drop, including reactors, heat exchangers, separators, piping and control valves, of the plant.

The discharge stream 12 from the compressor, together with the fresh hydrogen stream 2, constitutes the overall reaction gas 13 used in the hydrogenation reactors.

Figure 2:
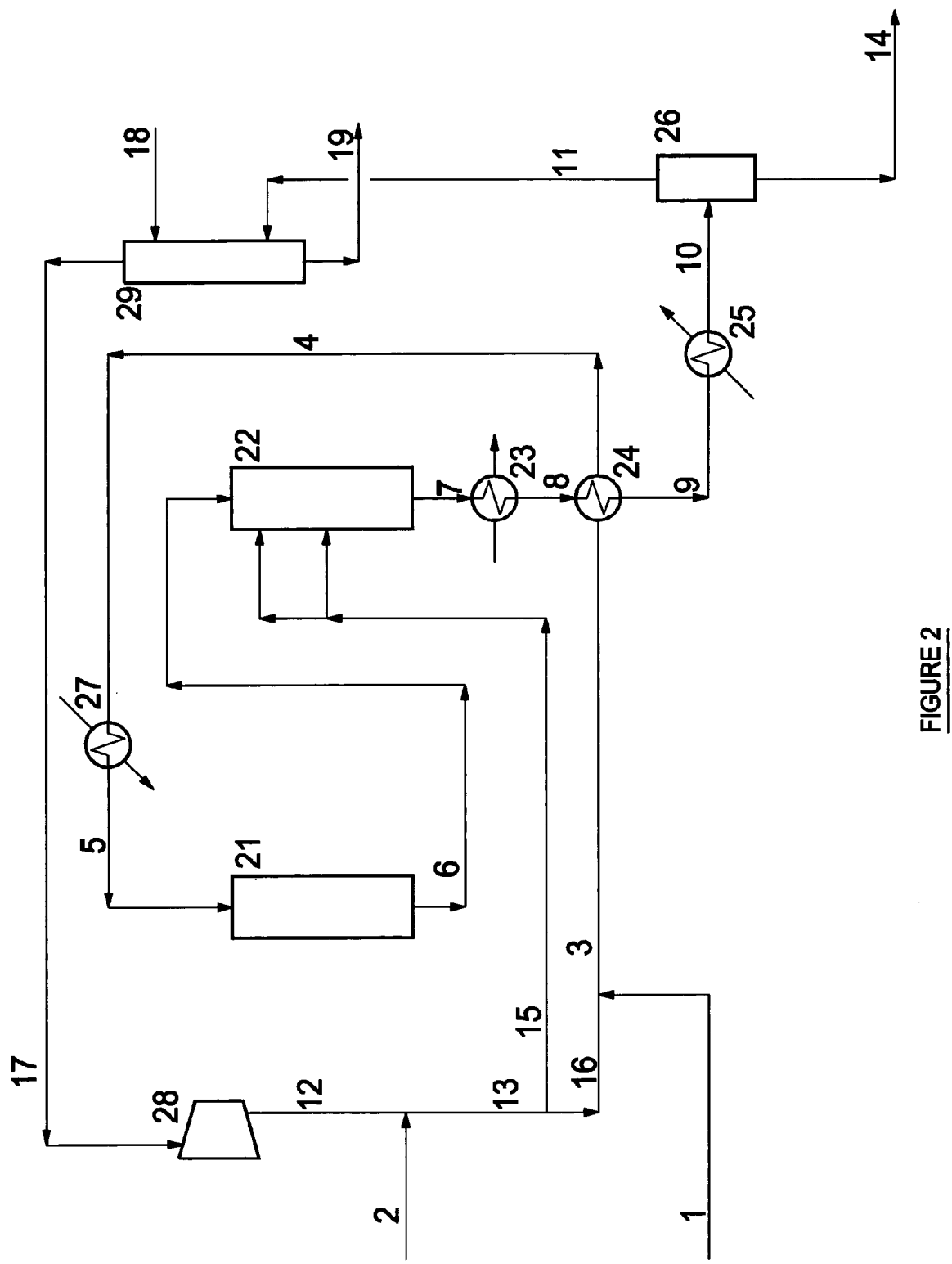
FIG. 2 is a more complete arrangement of the hydrogenation system, where besides the two stages of reaction, the following additional features are included:
(i) the temperature profile of the second stage of reaction is flattened by injection of cold recycle gas rich in hydrogen
(ii) the recycle gas is washed in an absorption column to reduce its moisture content, for increasing the tetrahydrofuran formation The present invention will be described with reference to these drawings.

FIG. 2 illustrates a plant for the production of BDO and, optionally GBL and THF, by catalytic reaction of a dialkyl maleate, where (i) the temperature profile of the second stage of reaction is flattened by injection of cold recycle gas rich in hydrogen and (ii) the recycle gas is washed in an absorption column to reduce its moisture content, by increasing the tetrahydrofuran formation.

The dimethyl maleate, produced by catalytic esterification of maleic anhydride, is fed as stream 1 in liquid phase. Stream 1 may also contain, beside DMM, a minor amount of unconverted DMS recycled back from the purification section of the plant, normally in mixture with some amount of GBL. Stream 1 is mixed with stream 16, which represents part of the mixture 13 of the fresh hydrogen stream 2 with the reaction recycle gas stream 12. Another minor portion of the recycle gas, as stream 15, is directly recycled at cold temperature to the second stage of reaction to control its temperature increase. FIG. 2 shows two different injection points: depending on reactor conditions, the points of injection could be more than two or even a single injection.

The stream 3, resulting from the mixture of fresh feed and recycle gas, is therefore a mixed liquid/vapor fluid. It is first preheated in the heat exchanger 24, by recovering heat from the effluent stream 8 of the second stage hydrogenation reactor 22, and then in the heat exchanger 27, using condensing low pressure steam as heating medium. This heat exchanger 27 is used for temperature control reason particularly during the start-up of the plant; during the normal steady operation of the plant, it could be disconnected or by-passed. By using peculiar start-up procedures, the heat exchanger 27 could be even eliminated. The outlet stream 5 from the exchanger enters the first stage of reaction 21. It is a downflow fixed bed adiabatic reactor, containing a specific catalyst highly selective for the saturation of the carbon double bond contained in the dialkyl maleate.

In the catalyst bed of reactor 21 the dimethylmaleate is transformed in dimethyl-succinate with very high conversion and selectivity. This reaction is highly exothermic and therefore the outlet temperature of the effluent stream 6 is somewhat higher than the temperature of the inlet stream 5. In a preferred embodiment of this invention, the reaction system is designed in a way that the outlet temperature of the first reactor stage matches the inlet temperature of the second reaction stage and, therefore, no heat exchanger is included in the design of the system.

The effluent from the reactor first stage 6 under controlled temperature enters the second stage reactor 22. It is also a downflow fixed bed adiabatic reactor, containing a catalyst different from the first stage and, more specifically, a catalyst suitable for the hydrogenolysis of the dimethyl succinate to 1,4-butanediol; depending from the conditions of pressure and temperature, together with BDO, variable amounts of gamma-butyrolactone and/or tetrahydrofuran can be produced.

Product stream 7 from the reactor is first cooled in the heat exchanger 23. The heat exchanger 23 is a steam generator, preferably of the kettle type with the production of steam inside the shell of the exchanger. It could be, as alternate case, a natural circulation exchanger, where the boiler feed water used to produce steam is fed to an external vessel and a natural thermosiphon circulation is generated between the vessel and the boiler.

The outlet stream 8 from the heat exchanger 23 is passed to the already described interexchanger 24. The outlet stream 9 is further cooled in the heat exchanger 25, which is without distinction a water cooler or an air cooler.

The cooled stream 10 enters the separator vessel 26, where the crude liquid product 14, containing mostly BDO with lower percentages of gamma-butyrolactone, tetrahydrofuran, methanol, water, unreacted dimethyl succinate and impurities, is separated from the vapor phase stream 11, consisting essentially in hydrogen, with lower amounts of methanol, tetrahydrofuran and water.

The gaseous stream 11, containing some percentages of moisture produced in the second stage of reaction, enters an absorption column 29, including trays or packing of different types, where the moisture is removed by contacting with a cold liquid stream 18, preferably consisting in purified GBL or BDO, fed to the top of the column. The resulting liquid stream 19 from the column bottom, consisting in wet GBL or BDO, joins the stream 14, to be sent together to the distillation section of the plant.

The dry gaseous stream 17 from the column overhead is then recycled back via the compressor 28, which differential pressure corresponds to the total pressure drop, including reactors, heat exchangers, columns, separators, piping and control valves, of the plant.

The discharge stream 12 from the compressor, together with the fresh hydrogen stream 2, constitutes the overall reaction gas 13 used in the hydrogenation reactors.

EXAMPLES

Experimental Apparatus

The laboratory scale experiments highlight the nature of the invention, but are not intended to limit its scope.

In these laboratory experiments, the hydrogenation of dimethyl maleate (DMM) to butanediol (BDO) has been produced by using two reactors in series: the first to convert DMM to dimethyl succinate (DMS), the second to convert DMS to BDO.

The first reactor consists of a stainless steel tube (1000 mm length, 20 mm internal diameter) externally thermo-controlled by heating bands. The reactor has been designed to contain a single catalytic bed for the hydrogenation of dimethyl maleate (DMM) to dimethyl succinate (DMS), with height of 60 mm and consisting of Pd supported by carbon.

The second reactor consists of a stainless steel tube (1800 mm length, 20 mm internal diameter) externally thermo-controlled by heating bands. For the tests described in this patent, it has been used with a single catalytic bed for the hydrogenolysis of the DMS to butanediol (BDO) with height of 600 mm. The catalysts used in the tests are based on copper, such as copper-chromite catalysts or copper-zinc oxide catalysts.

Both catalytic beds are preceded by a bed of glass cylinders (5×10 mm) with height of around 500 mm, used to preheat the feedstock to the reaction starting temperature.

The preheating of the liquid feed is performed by means of the crossing of the feedstock capillary tube through the heating bands of the first reactor.

The continuous monitoring of the temperature is performed by means of four thermocouples located respectively at the inlet and outlet of each catalytic bed.

The reaction products are recovered in two separated vessels, the first for the heavier product, directly located at the bottom of the second reactor, the second, mainly for the lighter products, located downstream of a double pipe heat exchanger for the cooling of the outlet mixture.

The samples were analyzed using a gas chromatograph equipped with a mass spectrometer detector (Agilent 5893N).

Example 1

In this example 1 only the first reactor was used.

A stream of liquid DMM was fed to the first reactor with Palladium on carbon catalyst, under the following conditions:
Pressure: 60 barg
Temperature: 100 to 165° C.
Molar ratio $H_2$/DMM: 50
Liquid hourly Space Velocity: about 2

The main results of tests at different temperatures are shown in Table 2

TABLE 2

| DMM Hydrogenation to DMS | | |
|---|---|---|
| Temperature ° C. | Conversion % | Selectivity to DMS % |
| 100 | 100 | 99.0 |
| 120 | 100 | 98.9 |
| 165 | 100 | 99.0 |

This example 1 shows the catalyst for the first step of reaction has both the necessary characteristics: i) high selectivity to the saturation of the carbon double bond and very low selectivity to the hydrogenolysis, ii) high activity to the saturation of the carbon double bond even at moderate temperature.

Even if, due to the small size of the laboratory equipment, the fully adiabatic conditions were not reproduced, a computer simulation of the conditions used during the test showed the increment of temperature from the inlet to the outlet of an adiabatic fixed bed reactor is around 60° C.

Example 2

In this example 2 both reactor stages, as described in the Experimental apparatus, were used.

A stream of liquid DMM was fed to the first reactor with palladium on carbon catalyst, under the following conditions:
Pressure: 70 barg
Temperatures:
 First stage outlet 130 to 135° C.
 Second stage outlet 178 to 182° C.
Molar ratio $H_2$/DMM: 50
Liquid hourly Space Velocity:
 First stage 2.0 $hr^{-1}$
 Second stage 0.2 $hr^{-1}$
The main results of the analytical test are shown in Table 3

TABLE 3

| DMM Hydrogenation and Hydrogenolysis-Dry conditions | |
|---|---|
| DMM conversion | 100% |
| Selectivity to BDO/GBL/THF | 95 |
| Composition (*) | % |
| THF | 13.09 |
| BuOH | 1.61 |
| 2Me THF | less than 0.01 |
| Me-butyrate | 0.47 |
| 2-Metoxy-THF | less than 0.01 |
| 4-Metoxy-BuOH | 0.44 |
| GBL | 4.86 |
| 1,4 BDO | 77.00 |
| DMS | 2.36 |
| Unknown 1 | 0.17 |
| Other unknown | less than 0.01 |

(*) net of water and methanol

Example 3

In this example 3 the conditions of example 2 have been repeated, with the only difference of a small addition of water to the feed to simulate the conditions of an industrial plant, where the recycle gas is saturated by water.

The main results of the analytical test are shown in Table 4

TABLE 4

| DMM Hydrogenation and Hydrogenolysis-Wet conditions | |
| --- | --- |
| DMM conversion | 100% |
| Selectivity to BDO/GBL/THF | 95.6 |

| Composition (*) | % |
| --- | --- |
| THF | 6.34 |
| BuOH | 0.69 |
| 2Me THF | less than 0.01 |
| Me-butyrate | 0.22 |
| 2-Metoxy-THF | less than 0.01 |
| 4-Metoxy-BuOH | 0.31 |
| GBL | 5.33 |
| 1,4 BDO | 83.96 |
| DMS | 2.20 |
| Unknown 1 | 0.95 |
| Other unknown | less than 0.01 |

(*) net of water and methanol

This example 3 shows that in wet conditions the overall results are very similar to the dry conditions ones, with the main difference in the yields in THF which drops from 13% to around 6%, being this difference compensated by an equivalent increased yield in BDO.

The overall yield in the three valuable products, BDO, GBL and THF, is 95.6%. Considering that the unreacted DMS may be separated by distillation, alone or in mixture with GBL, and recycled back to the reaction system, the actual overall yield is around 97.8%.

The invention claimed is:

1. A process for manufacturing, from dialkyl maleates and hydrogen, 1,4-butanediol and optionally, gamma-butyrolactone and/or tetrahydrofuran, said process comprising the following steps:
    a) hydrogenating a stream of dialkyl maleate in a first stage of reaction over suitable catalyst to produce dialkyl succinate;
    b) further hydrogenating the dialkyl succinate in a second stage of reaction, by using a different suitable catalyst, for producing mainly 1,4-butanediol, together with gamma-butyrolactone and tetrahydrofuran as co-products;
    wherein,
    the catalyst used in the first stage of reaction is a low content palladium catalyst supported on carbon or on alumina,
    the catalyst used for hydrogenolysis in the second stage is a copper containing catalyst, selected from a copper-chromite catalyst and a copper-zinc oxide catalyst,
    the first stage of reaction operates from 80 to 130° C. as an inlet temperature and from 160 to 190° C. as an outlet temperature, from 30 to 80 bar as pressure and with a liquid hourly space velocity from 0.5 to 2.0 hr$^{-1}$,
    the second stage of reaction operates from 160 to 190° C. as an inlet temperature, from 30 to 80 bar as pressure and with a liquid hourly space velocity from 0.1 to 0.3 hr$^{-1}$, and the catalyst of the second stage, in addition to copper-chromite or copper-zinc oxides, contains 2 to 15% of barium or manganese oxide, and
    the hydrogen/organic feed molar ratio is from 30 to 60, in order to obtain that:
(i) in both stages of reaction the conditions, as hydrogen/organic feed ratio, pressure and temperature, are such to maintain the reactors in mixed liquid/vapor phase,
(ii) the outlet temperature from first reaction step matches the inlet temperature of the second stage of the reaction, being all the heat of reaction of the first hydrogenation step used for pre-heating at the proper temperature the reactive mixture entering the second stage,
(iii) the heat content of the liquid-gas mixture from the second stage of reaction, is first used to generate low pressure steam and then to preheat the mixed feed to the inlet temperature of the first reaction stage, and
(iv) no external heat source is needed in the reaction system.

2. The process according to claim 1, wherein the operation is performed on a continuous basis.

3. The process according to claim 1, wherein the dialkyl maleate is dimethyl maleate.

4. The process according to claim 1, wherein both reaction stages are fixed bed adiabatic reactors.

5. The process according to claim 1, wherein the tetrahydrofuran/1,4-butanediol ratio may be modified by cooling the effluent from the second stage of reaction at a temperature between 20 to 60° C., by separating the resulting liquid and gaseous phases in a dedicated vessel, by recirculating the gaseous phase through a recycle compressor and by removing the water from said recycle gas by contact with a solid adsorbent or by contact in a absorption column with an organic solvent having high boiling point and hygroscopic tendency.

6. The process according to claim 5, wherein the organic solvent is gamma-butyrolactone or butanediol.

7. The process according to claim 1, wherein the tetrahydrofuran/1,4-butanediol ratio may be modified by subjecting either the crude or the refined butanediol to a process of dehydration at moderate temperature, 120 to 250° C., which may occur by contact with an acidic catalyst of the silica-alumina type.

8. The process according to claim 1, wherein the tetrahydrofuran+gamma-butyrolactone/1,4-butanediol ratio may be increased by operating the process at a pressure of the hydrogenation reaction in the range between 30 to 40 bar.

* * * * *